(12) United States Patent
Wang et al.

(10) Patent No.: US 11,879,131 B2
(45) Date of Patent: Jan. 23, 2024

(54) **USE OF ZMSBP12 GENE IN REGULATION OF DROUGHT RESISTANCE, PLANT HEIGHT, AND EAR HEIGHT OF *ZEA MAYS* L**

(71) Applicants: SOUTH CHINA AGRICULTURAL UNIVERSITY, Guangzhou (CN); BIOTECHNOLOGY RESEARCH INSTITUTE, CHINESE ACADEMY OF AGRICULTURAL SCIENCES, Beijing (CN)

(72) Inventors: Haiyang Wang, Guangzhou (CN); Yurong Xie, Beijing (CN); Bingbing Zhao, Beijing (CN); Baobao Wang, Beijing (CN); Yongping Zhao, Beijing (CN); Dexin Kong, Guangzhou (CN); Quanquan Li, Beijing (CN); Yaoyao Li, Guangzhou (CN)

(73) Assignees: SOUTH CHINA AGRICULTURAL UNIVERSITY, Guangzhou (CN); BIOTECHNOLOGY RESEARCH INSTITUTE, CHINESE ACADEMY OF AGRICULTURAL SCIENCES, Beijing (CN)

( * ) Notice: Subject to any disclaimer, the term of this patent is extended or adjusted under 35 U.S.C. 154(b) by 0 days.

(21) Appl. No.: 17/907,408

(22) PCT Filed: Oct. 21, 2020

(86) PCT No.: PCT/CN2020/122356
§ 371 (c)(1),
(2) Date: Sep. 27, 2022

(87) PCT Pub. No.: WO2021/189832
PCT Pub. Date: Sep. 30, 2021

(65) Prior Publication Data
US 2023/0117599 A1    Apr. 20, 2023

(30) Foreign Application Priority Data
Mar. 27, 2020    (CN) .......................... 202010232213.2

(51) Int. Cl.
*C12N 15/82*    (2006.01)
(52) U.S. Cl.
CPC ..... *C12N 15/8273* (2013.01); *C12N 15/8262* (2013.01)
(58) Field of Classification Search
None
See application file for complete search history.

(56) References Cited

U.S. PATENT DOCUMENTS 6,162,965 A * 12/2000 Hansen .................. C12N 1/205
800/278
2006/0123505 A1    6/2006 Kikuchi et al.

FOREIGN PATENT DOCUMENTS

| CN | 106062195 A | 10/2016 |
|---|---|---|
| CN | 111763682 A | 10/2020 |
| WO | 2016127075 A2 | 8/2016 |

OTHER PUBLICATIONS

Yilmaz et al. (NCBI,GenBank Sequence Accession No. NM_001136780, Published Apr. 22, 2017).*
Peng et al. (Genetics and Molecular Biology, 42(2):380-394, Published Dec. 31, 2019).*
Wei et al. ( Journal of Experimental Botany, vol. 69(20: 4675-4688, published Jul. 10, 2018).*
Wei et al. ( Journal of Experimental Botany, vol. 69(20: 4675-4688, published Jul. 10, 2018, including supplementary table 1).).*
Yilmaz et al. (Genbank Sequence Accession No. NM_001136780, Published Apr. 22, 2017).*
Ranocha et al. (Plant Physiol., 129(1):145-155, 2002).*
Mark A. Batzer, et al., Enhanced evolutionary PCR using oligonucleotides with inosine at the 3'-terminus, Nucleic Acids Research, 1991, pp. 5081, vol. 19, No. 18.
Eiko Ohtsuka, et al., An Alternative Approach to Deoxyoligonucleotides as Hybridization Probes by Insertion of Deoxyinosine at Ambiguous Codon Positions, The Journal of Biological Chemistry, 1985, pp. 2605-2608, vol. 260, No. 5.
Gian Maria Rossolini, et al., Use of deoxyinosine-containing primers vs degenerate primers for polymerase chain reaction based on ambiguous sequence information, Molecular and Cellular Probes, 1994, pp. 91-98, vol. 8.
Xiaojian Peng, et al., Comparative genome analysis of the SPL gene family reveals novel evolutionary features in maize, Genetics and Molecular Biology, 2019, pp. 380-394, vol. 42, No. 2.
Hongbin Wei, et al., Exploiting SPL genes to improve maize plant architecture tailored for high-density planting, Journal of Experimental Botany, 2018, pp. 4675-4688, vol. 69, No. 20.

(Continued)

*Primary Examiner* — Vinod Kumar
(74) *Attorney, Agent, or Firm* — Bayramoglu Law Offices LLC

(57) ABSTRACT

A use of a ZmSBP12 gene in the regulation of drought resistance, plant height, and ear height of *Zea mays* L. is provided. After the ZmSBP12 gene is over-expressed in *Zea mays* L., the resulting *Zea mays* L. mutant plant exhibits increased drought resistance and decreased plant and ear heights. The overexpression of the ZmSBP12 gene leads to increased drought resistance and decreased plant and ear heights, indicating that the ZmSBP12 gene plays a crucial role in the drought resistance and plant type (plant height) of *Zea mays* L. The expression abundance of the ZmSBP12 gene is increased to improve the drought resistance of *Zea mays* L. and reduce the plant and ear heights of *Zea mays* L., which can be used for the assisted breeding of novel drought-resistant and lodging-resistant *Zea mays* L. varieties and the breeding of excellent inbred lines and hybrids of *Zea mays* L.

6 Claims, 4 Drawing Sheets

Specification includes a Sequence Listing.

(56) References Cited

OTHER PUBLICATIONS

Hu-De Mao, et al., Genome-wide analysis of the SPL family transcription factors and their responses to abiotic stresses in maize, Plant Gene, 2016, pp. 1-12, vol. 6.

Kuyang Liu, et al., Genome-wide identification and comparative analysis of drought-related microRNAs in two maize inbred lines with contrasting drought tolerance by deep sequencing, PLOS ONE, 2019, pp. 1-22, vol. 14, No. 7: e0219176.

Zhang Wei, et al., Genome-wide identification, phylogeny and expression analysis of the SBP-box gene family in maize (*Zea mays*), Journal of Integrative Agriculture, 2016, pp. 29-41, vol. 15, No. 1.

Yilmaz A, et al., NM_001136780.1, *Zea mays* SBP-transcription factor 12 (sbp12), mRNA, GenBank, 2020.

Yilmaz A, et al., NP_001130252.1, SBP-transcription factor 12 [*Zea mays*], GenPept, 2020.

\* cited by examiner

SEQUENCE LISTING

<160> NUMBER OF SEQ ID NOS: 10

<210> SEQ ID NO 1
<211> LENGTH: 332
<212> TYPE: PRT
<213> ORGANISM: Zea mays L.

<400> SEQUENCE: 1

Met Glu Trp Thr Ala Pro Lys Pro Ala Ser Ser Pro Pro Leu Leu Trp
1               5                   10                  15

Asp Trp Gly Asp His Ala Ala Thr Gly Ser Gly Ser Ser Ser Asp Ala

```
                20              25              30
Pro Ala Arg Arg Gly Gly Lys Glu Arg Glu Ala Lys Arg Ala Arg Ala
             35              40              45
Gly Glu Asp Arg Gly Gly Glu Leu Arg Cys Gln Val Glu Gly Cys
         50              55              60
Gly Leu Asp Leu Ser Arg Val Lys Asp Tyr His Arg Lys His Arg Val
 65              70              75              80
Cys Glu Ala His Thr Lys Ser Pro Arg Val Ile Val Ala Gly Gln Glu
                 85              90              95
Arg Arg Phe Cys Gln Gln Cys Ser Arg Phe His Ala Leu Ser Glu Phe
             100             105             110
Asp Gln Lys Lys Arg Ser Cys Arg Arg Leu Ser Asp His Asn Ala
             115             120             125
Arg Arg Arg Lys Pro Gln Pro Asp Ala Phe Thr Phe Ala Ser Ala Lys
     130             135             140
Leu Pro Ser Thr Leu Phe Asp Asp Arg Arg Gln Ile Ser Phe Val Trp
145             150             155             160
Asn Lys Ala Pro Val Ser His Val Arg Pro Phe Thr Ser Pro Trp Asp
                 165             170             175
Ser Ser Ser Asp Leu Lys Pro Pro Tyr Ala Lys Glu Ile Ser Asp Val
             180             185             190
Ser Thr Lys Val Gly Thr Ile Thr Gly Gln Val His Leu Asp Lys Ser
             195             200             205
His Met Phe Asn Ala Ile Pro Thr Leu Ser His Gly Lys Asp Glu Pro
     210             215             220
Trp Pro Met Lys Gly Leu Asp Met Ser Ile Ser Ala Ser Lys Phe Asp
225             230             235             240
Gly Ala Ala Asp Leu Gln His Ala Leu Ser Leu Leu Ser Ala Gly Ala
                 245             250             255
Cys Gly Leu Pro Asp Ser Val His Gln Thr Ser Cys Ile Ile Gln Phe
             260             265             270
Asn Gly Ala Ser Glu Asn Ser Ser Asp Leu His Val Thr His Gly Arg
             275             280             285
Asn Ser Gly Pro Ala Ser Cys Ala Asp Ala Gln His Ile Ala Ala Gln
     290             295             300
Pro Gln Ser Gln Leu Phe His Phe Thr Thr Asp Thr Gly Asn Thr Val
305             310             315             320
Tyr Glu Pro Ser Phe Phe Gly Val Asn Gln Ile Asn
                 325             330

<210> SEQ ID NO 2
<211> LENGTH: 999
<212> TYPE: DNA
<213> ORGANISM: Zea mays L.

<400> SEQUENCE: 2
atggagtgga cggccccgaa gcccgcctca tcgcctcccc tcctctggga ctggggagac    60
cacgccgcca cgggctcggg ctcctccagc gacgccccgg cgcggcgcgg cgggaaggag   120 cggaggcga agcgtgccag gccggcgag accgcggg gaggtgagct gaggtgccag       180 gtcgagggt gcggattgga cctcagcagg gtcaaggact accaccgtaa gcaccgcgtc   240
tgcgaggccc acaccaagtc ccccgcgtc atcgtcgccg gccaggagcg ccggttctgc    300
cagcagtgca gccgattcca tgcgctgtca gagtttgatc agaagaagag gagctgcagg  360
```

```
aggcgtctgt ctgatcacaa tgcccgccgc cggaagcctc agccagatgc attcaccttc    420
gcctctgcaa agctgccttc gacattgttt gatgataggc ggcaaataag ttttgtctgg    480
aataaagctc ctgttagcca tgtaagaccc ttcacttctc catgggacag ctcatctgac    540
ttaaagcccc cttatgcaaa ggaaataagt gatgtatcaa caaaagttgg gacaattact    600
ggacaagttc atttggataa atctcacatg ttcaatgcta ttccaacact tagccatggc    660
aaagatgagc cttggccaat gaaggtctg gacatgtcta tatctgcttc aaaattcgat     720
ggagcagcgg atcttcagca tgctctctct cttctgtcag ccggcgcttg tggactgcct    780
gattctgtac atcaaacatc ttgcattatc caattcaatg gtgccagcga gaacagcagt    840
gaccttcatg taacgcatgg caggaactct ggtccagcat catgcgccga tgcgcagcat    900
atagctgccc agcctcagtc tcagctgttt cattttacca cagataccgg caatactgtt    960
tatgagccca gtttctttgg tgtaaaccag ataaattaa                           999
```

<210> SEQ ID NO 3
<211> LENGTH: 22
<212> TYPE: DNA
<213> ORGANISM: Artificial Sequence
<220> FEATURE:
<223> OTHER INFORMATION: The sequence is synthetized.

<400> SEQUENCE: 3

```
agctcatctg acttaaagcc cc                                              22
```

<210> SEQ ID NO 4
<211> LENGTH: 21
<212> TYPE: DNA
<213> ORGANISM: Artificial Sequence
<220> FEATURE:
<223> OTHER INFORMATION: The sequence is synthetized.

<400> SEQUENCE: 4

```
ttcattggcc aaggctcatc t                                               21
```

<210> SEQ ID NO 5
<211> LENGTH: 155
<212> TYPE: DNA
<213> ORGANISM: Zea mays L.

<400> SEQUENCE: 5

```
agctcatctg acttaaagcc cccttatgca aaggaaataa gtgatgtatc aacaaaagtt     60
gggacaatta ctggacaagt tcatttggat aaatctcaca tgttcaatgc tattccaaca   120
cttagccatg gcaaagatga gccttggcca atgaa                              155
```

<210> SEQ ID NO 6
<211> LENGTH: 996
<212> TYPE: DNA
<213> ORGANISM: Artificial Sequence
<220> FEATURE:
<223> OTHER INFORMATION: The sequence is synthetized.

<400> SEQUENCE: 6

```
atggagtgga cggccccgaa gcccgcctca tcgcctcccc tcctctggga ctggggagac     60
cacgccgcca cgggctcggg ctcctccagc gacgccccgg cgcggcgcgg cgggaaggag   120 cggggaggcga agcgtgccag ggccggcgag gaccgcgggg gaggtgagct gaggtgccag   180 gtcgagggt gcggattgga cctcagcagg gtcaaggact accaccgtaa gcaccgcgtc   240
tgcgaggccc acaccaagtc cccccgcgtc atcgtcgccg gccaggagcg ccggttctgc   300
```

```
cagcagtgca gccgattcca tgcgctgtca gagtttgatc agaagaagag gagctgcagg      360
aggcgtctgt ctgatcacaa tgcccgccgc cggaagcctc agccagatgc attcaccttc      420
gcctctgcaa agctgccttc gacattgttt gatgataggc ggcaaataag ttttgtctgg      480
aataaagctc ctgttagcca tgtaagaccc ttcacttctc catgggacag ctcatctgac      540
ttaaagcccc cttatgcaaa ggaaataagt gatgtatcaa caaagttgg gacaattact       600 ggacaagttc atttggataa atctcacatg ttcaatgcta ttccaacact tagccatggc      660
aaagatgagc cttggccaat gaaaggtctg gacatgtcta tatctgcttc aaaattcgat      720
ggagcagcgg atcttcagca tgccctgagc ctgctcagcg ccggcgcttg tggactgcct      780
gattctgtac atcaaacatc ttgcattatc caattcaatg gtgccagcga gaacagcagt      840
gaccttcatg taacgcatgg caggaactct ggtccagcat catgcgccga tgcgcagcat      900
atagctgccc agcctcagtc tcagctgttt cattttacca cagataccgg caatactgtt      960
tatgagccca gtttctttgg tgtaaaccag ataaat                                996

<210> SEQ ID NO 7
<211> LENGTH: 21
<212> TYPE: DNA
<213> ORGANISM: Artificial Sequence
<220> FEATURE:
<223> OTHER INFORMATION: The sequence is synthetized.

<400> SEQUENCE: 7
catgctctct ctcttctgtc a                                                21

<210> SEQ ID NO 8
<211> LENGTH: 78
<212> TYPE: DNA
<213> ORGANISM: Artificial Sequence
<220> FEATURE:
<223> OTHER INFORMATION: The sequence is synthetized.

<400> SEQUENCE: 8
gtttggtgtt acttctgcag atggagtgga cggccccgaa gctgagcagg ctcagggcat      60
gctgaagatc cgctgctc                                                    78

<210> SEQ ID NO 9
<211> LENGTH: 84
<212> TYPE: DNA
<213> ORGANISM: Artificial Sequence
<220> FEATURE:
<223> OTHER INFORMATION: The sequence is synthetized.

<400> SEQUENCE: 9
gccctgagcc tgctcagcgc cggcgcttgt ggactgcctg atttgccacc accggatcca      60
tttatctggt ttacaccaaa gaaa                                             84

<210> SEQ ID NO 10
<211> LENGTH: 81
<212> TYPE: DNA
<213> ORGANISM: Artificial Sequence
<220> FEATURE:
<223> OTHER INFORMATION: The sequence is synthetized.

<400> SEQUENCE: 10
gtttggtgtt acttctgcag atggagtgga cggccccgaa tgccaccacc ggatccattt      60
atctggttta caccaaagaa a                                                81
```

USE OF ZMSBP12 GENE IN REGULATION OF DROUGHT RESISTANCE, PLANT HEIGHT, AND EAR HEIGHT OF ZEA MAYS L

CROSS REFERENCE TO THE RELATED APPLICATIONS

This application is the national phase entry of International Application No. PCT/CN2020/122356, filed on Oct. 21, 2020, which is based upon and claims priority to Chinese Patent Application No. 202010232213.2, filed on Mar. 27, 2020, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBBJSY008-PKG Sequence Listing.txt, created on Sep. 20, 2022, and is 7,935 bytes in size.

TECHNICAL FIELD

The present disclosure relates to a novel use of a ZmSBP12 gene and more particularly to a novel use of a ZmSBP12 gene in the regulation of drought resistance, plant height, and ear height of *Zea mays* L. and belongs to the field of use of the ZmSBP12 gene in *Zea mays* L. breeding.

BACKGROUND

*Zea mays* L. has become China's first grain crop with an annual planting area of 500 million mu. As a big agricultural producer, China faces the problem that 22% of the world's population needs to be fed with 7% of the world's land, and in recent years, China's dependence on imported corn has been increasing, causing a serious potential food safety risk. Therefore, there is an urgent need to develop a hybrid with strong stress resistance (drought resistance), lodging resistance, and high yield potential.

Drought is an important environmental factor affecting the stable production of *Zea mays* L. in China and the world. Arid and semi-arid areas make up about 34.9% of the global land area and 42.9% of the cultivated area. The annual decrease in grain output caused by drought accounts for about 60% of grain loss, and the remaining grain loss is caused by various other natural disasters. Nearly 70% of the *Zea mays* L. planting area in China is distributed in the hilly drylands or plain drylands that rely on natural rainfall in Northeast China, North China, Southwest China, and Northwest China. In Jilin province with the largest *Zea mays* L. planting area, the output is reduced by 25% or more in general drought years, the output is reduced by 30% to 35% in severe drought years, and there is almost no harvest in some regions in extremely-severe drought years. Therefore, screening genotypes with efficient utilization of nutrients and water and breeding new water and fertilizer resource-saving and environmentally-friendly varieties have become urgent requirements for corn production and important goals for drought-resistant breeding in China. In addition, with global warming and environmental deterioration, more places will be threatened by drought. Thus, it is necessary to accelerate the research on drought resistance of *Zea mays* L. and other crops.

At present, the research on drought resistance of *Zea mays* L. is not perfect, and only a few genes, such as ZmVPP1, have application potential. Long-term corn production practice shows that the cultivation of a new dwarf and density-resistant *Zea mays* L. variety suitable for mechanized operation is another key technical measure to increase output and efficiency. It has been reported that increased plant height means more photosynthate is being used for vegetative growth instead of reproductive growth, which directly affects corn output. The increased plant height also increases the gravity center of *Zea mays* L., which is accompanied by spindly growth, stalk thinning, vascular bundle reduction, changes in the composition and content of lignocellulose in a cell wall, and reduction in mechanical strength of a stalk, which further aggravates the occurrence of lodging. Therefore, effectively reducing a plant's height is a basic requirement for cultivating a new *Zea mays* L. variety with a high and stable yield. The utilization of semi-dwarfing genes sd1 and rht1 in *Oryza sativa* L. and *Triticum aestivum* L. directly leads to the first green revolution and greatly improves crop output. However, a major semi-dwarfing gene that is similar to such a green revolution gene and can effectively reduce a plant's height without an obvious negative effect on the ear has not yet been found in *Zea mays* L.

A ZmSBP12 gene is a *Zea mays* L. SQUAMOSA-PROMOTER BINDING PROTEIN-LIKE (SPL) transcription factor regulated by miR156. The ZmSBP12 gene has 4 exons and 3 introns, and the main functional regions thereof include a miR156 regulatory site (CATGCTCTCTCTCTTCTGTCA, as shown in SEQ ID NO: 7) and an SBP domain.

The drought resistance, plant height, and ear height of *Zea mays* L. are all often controlled by many minor quantitative trait loci (QTLs), and in the current *Zea mays* L. breeding, it is still necessary to continuously accumulate these minor QTLs to improve the drought resistance and reduce the plant and ear heights, which has low selection efficiency. Therefore, it is of great theoretical and practical significance to mine for the major genes for controlling the drought resistance, plant height, and ear height of *Zea mays* L. and analyze a corresponding genetic regulation network.

SUMMARY

A major objective of the present disclosure is to provide a use of a ZmSBP12 gene in the regulation of drought resistance, plant height, and ear height of *Zea mays* L.

The above objective of the present disclosure is achieved by the following technical solutions.

In the present disclosure, after the ZmSBP12 gene is over-expressed in *Zea mays* L., the resulting *Zea mays* L. mutant plant exhibits increased drought resistance and decreased plant and ear heights. The overexpression of the ZmSBP12 gene leads to increased drought resistance and decreased plant and ear heights, indicating that the ZmSBP12 gene plays a crucial role in the drought resistance and plant type (plant height) of *Zea mays* L.

Therefore, the expression abundance of the ZmSBP12 gene in *Zea mays* L. can be changed to regulate the drought resistance, plant height, and ear height of *Zea mays* L. For example, the expression abundance of the ZmSBP12 gene in *Zea mays* L. can be increased to increase drought resistance and reduce the plant or ear height. On the contrary, the expression abundance of the ZmSBP12 gene in *Zea mays* L. can be reduced to reduce the drought resistance and increase the plant or ear height.

The present disclosure achieves the effects of improving the drought resistance and reducing the plant and ear heights for *Zea mays* L. by increasing the expression abundance of the ZmSBP12 gene. Therefore, all methods in which the mRNA and protein abundance of the ZmSBP12 gene are regulated to increase the drought resistance and reduce the plant and ear heights for *Zea mays* L. should fall within the protection scope of the present disclosure, and these methods should include all methods of artificially synthesizing and designing nucleotides or proteins and using unreported natural variations.

Those skilled in the art can use various conventional technical means to increase the expression abundance of the ZmSBP12 gene in *Zea mays* L. and reduce the expression abundance of the ZmSBP12 gene in *Zea mays* L. For example, a ZmSBP12 gene overexpression vector is constructed, then the ZmSBP12 gene is over-expressed or super-expressed in *Zea mays* L. to improve the drought resistance of *Zea mays* L. or reduce the plant or ear height of *Zea mays* L., and then a transgenic plant with strong stress resistance (drought resistance) and lodging resistance is obtained through selective breeding; or the ZmSBP12 gene in a plant is subjected to a functional defect mutation through gene editing or gene knockout to obtain a transgenic plant with no drought resistance and increased plant and ear heights.

The present disclosure also relates to the use of the ZmSBP12 gene in *Zea mays* L. breeding, including a breeding process of a *Zea mays* L. inbred line or hybrid. Specifically, the overexpression of the ZmSBP12 gene in one of the parents for a *Zea mays* L. hybrid can reduce the plant and ear heights of *Zea mays* L. and improve the drought resistance of *Zea mays* L.

The present disclosure provides a method for improving drought resistance of *Zea mays* L. that includes: (1) constructing a recombinant plant expression vector carrying a ZmSBP12 gene; (2) transforming the constructed recombinant plant expression vector into a plant tissue or a plant cell; and (3) subjecting the ZmSBP12 gene to overexpression in the plant tissue or the plant cell.

The present disclosure also provides a method for improving the lodging resistance of *Zea mays* L. that includes: (1) constructing a recombinant plant expression vector carrying a ZmSBP12 gene; (2) transforming the constructed recombinant plant expression vector into a plant tissue or a plant cell; and (3) subjecting the ZmSBP12 gene to overexpression in the plant tissue or the plant cell.

The increasing the drought resistance and reducing the plant and ear heights for *Zea mays* L. in the present disclosure are reflected by the enhanced drought resistance and reduced plant and ear heights of a transgenic plant compared with a wild type (WT) plant under the same conditions.

The ZmSBP12 gene is operably connected to an expression regulatory element to obtain a recombinant plant expression vector that allows the expression of the coding gene in a plant. The recombinant plant expression vector may include a 5' non-coding region, a polynucleotide sequence shown in SEQ ID No: 2, and a 3' non-coding region. The 5' non-coding region may include a promoter sequence, an enhancer sequence, and/or a translation enhancer sequence. The promoter may be a constitutive promoter, inducible promoter, or tissue or organ-specific promoter. The 3' non-coding region may include a terminator sequence, an mRNA cleavage sequence, and the like. A suitable terminator sequence can be taken from a Ti-plasmid of *Agrobacterium tumefaciens* (*A. tumefaciens*), such as a termination region of octopine synthase (OCS) and nopaline synthase (NOS).

The recombinant plant expression vector may also include a selective marker gene for selecting transformed cells. The selective marker gene is provided to select transformed cells or tissues. The marker gene includes a gene conferring antibiotic resistance, a gene conferring herbicide resistance, and the like. In addition, the marker gene includes genes having phenotypic markers, such as β-galactosidase and fluorescent protein.

Moreover, those skilled in the art can optimize the polynucleotide sequence shown in SEQ ID No: 2 to enhance the expression efficiency in the plant. For example, a preferred codon of a target plant can be optimized and used to synthesize a polynucleotide sequence to enhance the expression efficiency in the target plant; or the polynucleotide sequence shown in SEQ ID No: 2 can be site-engineered to obtain an engineered variant. As a preferred embodiment, the variant has a polynucleotide sequence shown in SEQ ID No: 6.

The present disclosure also provides a recombinant plant expression vector carrying the ZmSBP12 gene and a host cell carrying the recombinant plant expression vector.

The ZmSBP12 gene in the present disclosure can encode an amino acid sequence shown in SEQ ID No: 1. Due to the specificity of the amino acid sequence, any fragment of a peptide protein including the amino acid sequence shown in SEQ ID NO: 1 or a variant thereof such as a conservative variant, a biologically-active fragment, or a derivative thereof shall fall within the protection scope of the present disclosure as long as the fragment of the peptide protein or the variant thereof has a sequence homology of 90% or more with the above-mentioned amino acid sequence. A specific alteration may include the deletion, insertion, or substitution of an amino acid in an amino acid sequence. For a conservative alteration of a variant, a substituted amino acid has a similar structure or similar chemical properties to the original amino acid, for example, isoleucine is substituted by leucine. The variant can also have a non-conservative alteration, for example, glycine is substituted by tryptophan.

The ZmSBP12 gene has a nucleotide sequence shown in SEQ ID No: 2. Due to the specificity of the nucleotide sequence, any variant of the polynucleotide sequence shown in SEQ ID NO: 2 shall fall within the protection scope of the present disclosure as long as the variant has a homology of 90% or more with the polynucleotide sequence. A variant of the polynucleotide sequence refers to a polynucleotide sequence obtained through one or more nucleotide alterations. The variant of the polynucleotide sequence can be a biotic or abiotic variant, including a substitution variant, a deletion variant, and an insertion variant. As known in the art, an allelic variant is an alternative form of a polynucleotide, which may involve a substitution, deletion, or insertion of a polynucleotide that does not substantially change the function of a peptide protein encoded thereby.

The present disclosure also relates to specific amplification primers for detecting an expression level of the ZmSBP12 gene, where the specific amplification primers respectively have nucleotide sequences shown in SEQ ID No: 3 and SEQ ID No: 4:

an upstream primer:
5'-AGCTCATCTGACTTAAAGCCCC-3' a downstream primer:
5'-TTCATTGGCCAAGGCTCATCT-3'

The specific amplification primers can be used to amplify a gene of Zea mays L., and a product fragment is 155 bp and has a sequence shown in SEQ ID No: 5.

The present disclosure can improve the drought resistance of Zea mays L. and reduce the plant and ear heights of Zea mays L. by increasing the expression abundance of the ZmSBP12 gene, which can be used for the assisted breeding of novel drought-resistant and lodging-resistant Zea mays L. varieties and can also be used for the breeding of excellent inbred lines and hybrids of Zea mays L.

Definitions of Terms Related to the Present Disclosure

Unless otherwise defined, all technical and scientific terms used herein have the same meanings as commonly understood by those of ordinary skill in the art to which the present disclosure belongs. Although any methods, devices, and materials similar or equivalent to those described herein can be used in the practice or test of the present disclosure, preferred methods, devices, and materials are now described.

The term "polynucleotide" or "nucleotide" refers to deoxyribonucleotide, deoxyriboside, riboside, or ribonucleotide and a polymer thereof in a single-stranded or double-stranded form. Unless otherwise specifically limited, the term encompasses nucleic acids with known analogs of natural nucleotides, and the analogs have binding properties similar to a reference nucleic acid and are metabolized in a manner similar to that of natural nucleotides. Unless otherwise specifically limited, the term also refers to oligonucleotide analogs, including peptide nucleic acids (PNAs) and DNA analogs used in antisense technology (organothiophosphate, phosphoramidate, and the like). Unless otherwise specified, a specific nucleic acid sequence also implicitly encompasses conservatively modified mutants (including, but not limited to, degenerate codon substitutions) and complementary sequences thereof and explicitly specified sequences. Specifically, a degenerate codon substitution can be achieved by generating a sequence in which one or more selected (or all) codons are subjected to position-3 substitution with mixed bases and/or deoxyinosine residues (Batzer et al., *Nucleic Acid Res.* 19: 5081 (1991); Ohtsuka et al., *J. Biol. Chem.* 260: 2605-2608 (1985); Rossolini et al., *Mol Cell. Probes* 8: 91-98 (1994)).

The terms "polypeptide", "peptide", and "protein" are used interchangeably herein to mean a polymer of amino acid residues. That is, the description for the polypeptide is also applicable to the peptide and protein, and vice versa. The terms apply to a natural amino acid polymer and an amino acid polymer in which one or more amino acid residues are non-naturally encoded amino acids. As used herein, the terms encompass amino acid chains of any length, including full-length proteins (namely, antigens) in which amino acid residues are linked through covalent peptide bonds.

The "variant" refers to a sequence substantially similar to the polynucleotide sequence of the present disclosure, and a variant is obtained through the deletion, insertion, and/or substitution of one or more nucleotides at one or more sites in a natural polynucleotide sequence. Conservative variants of the polynucleotide sequence of the present disclosure include those variants that do not alter the encoded amino acid sequence due to the degeneracy of the genetic code. Such natural variants can be identified by the existing molecular biology techniques. Variant polynucleotides also include synthetic polynucleotides, such as a polynucleotide variant obtained through site-directed mutagenesis that can still encode the amino acid sequence shown in SEQ ID No: 1 or a polynucleotide variant obtained through recombination (such as DNA shuffling). Those skilled in the art can screen or evaluate the function or activity of a protein encoded by a variant polynucleotide through the following molecular biotechnologies: DNA binding activity, interaction among proteins, activation of gene expression in transient studies, or expression effects in transgenic plants.

The "stringent hybridization conditions" in the present disclosure refer to low ionic strength and high-temperature conditions known in the art. Generally, under stringent conditions, a detectable degree of hybridization between a probe and a target sequence thereof is higher than a detectable degree of hybridization of the probe with other sequences (for example, at least 2 times more than the background). Stringent hybridization conditions are sequence-dependent and will be different under different environmental conditions, and long sequences are specifically hybridized at high temperatures. By controlling the stringency or washing conditions of hybridization, a target sequence that is 100% complementary to a probe can be identified. Detailed guidance on nucleic acid hybridization can refer to the relevant literature. More specifically, the stringent conditions usually involve a temperature about 5° C. to 10° C. lower than a thermal melting point ($T_m$) of a specific sequence at a specified ionic strength and pH. $T_m$ refers to a temperature at which 50% of a probe complementary to a target sequence is hybridized with the target sequence in an equilibrium state (at a specified ionic strength, pH, and nucleic acid concentration) (because the target sequence exists in excess, 50% of the probe is occupied in the equilibrium state at $T_m$). The stringent conditions can be as follows: the salt (sodium ion or other salts) concentration is lower than about 1.0 M (which is usually about 0.01 M to 1.0 M) at pH 7.0 to 8.3 and the temperature is at least about 30° C. for short probes (including, but not limited to, 10 to 50 nucleotides) and at least about 60° C. for long probes (including, but not limited to, more than 50 nucleotides). The stringent conditions can also be achieved by adding a destabilizer such as a formamide. For selective or specific hybridization, a positive signal can be at least twice that of the background hybridization, and optionally 10 times that of the background hybridization. Exemplary stringent hybridization conditions can be as follows: 50% formamide, 5×SSC, and 1% SDS, and incubation at 42° C.; or 5×SSC, 1% SDS, incubation at 65° C., washing in 0.2×SSC, and washing in 0.1% SDS at 65° C. The washing can be conducted for 5 min, 15 min, 30 min, 60 min, 120 min, or more.

In the present disclosure, the "more nucleotides" usually refers to 2 to 8 nucleotides and preferably 2 to 4 nucleotides. The "substitution" refers to the replacement of one or more amino acid residues with different amino acid residues. The "deletion" refers to the reduction in the number of amino acid residues, that is, the lack of one or more amino acid residues. The "insertion" refers to the change in a sequence of amino acid residues, and relative to natural molecules, the change results in the addition of one or more amino acid residues.

The term "recombinant host cell strain" or "host cell" refers to a cell with the polynucleotide of the present disclosure, regardless of the method used for insertion to produce a recombinant host cell, such as direct uptake, transduction, f-pairing, or other methods known in the art. The exogenous polynucleotide can be maintained as a non-integrated vector such as a plasmid or can be integrated into a host genome. The host cell can be a prokaryotic cell or a eukaryotic cell, and the host cell can also be monocotyledonous or dicotyledonous.

The term "operably linked" refers to a functional connection between two or more elements, and operably-linked elements may be contiguous or non-contiguous.

The term "transformation" refers to the genetic transformation of a polynucleotide or polypeptide into a plant by introducing a coding gene into a plant cell. Methods for introducing the polynucleotide or polypeptide into a plant are known in the art, including, but not limited to, stable transformation, transient transformation, virus-mediated transformation, and the like. The "stable transformation" means that an introduced polynucleotide construct is integrated into a genome of a plant cell and can be inherited by its progeny. The "transient transformation" means that the polynucleotide is introduced into a plant but can only be temporarily expressed or present in the plant.

The term "expression" refers to the transcription and/or translation of an endogenous gene or transgene in a plant cell.

The term "coding sequence" refers to a nucleic acid sequence that can be transcribed into RNA.

The term "recombinant plant expression vector" refers to one or more DNA vectors to achieve plant transformation, and these vectors are often referred to as binary vectors in the art. Binary vectors and vectors with helper plasmids are most commonly used for *A. tumefaciens*-mediated transformation. Binary vectors usually include cis-acting sequences required for T-DNA transfer, selective markers engineered to be expressed in plant cells, heterologous DNA sequences to be transcribed, and the like.

DETAILED DESCRIPTION OF THE EMBODIMENTS

Figure 1:
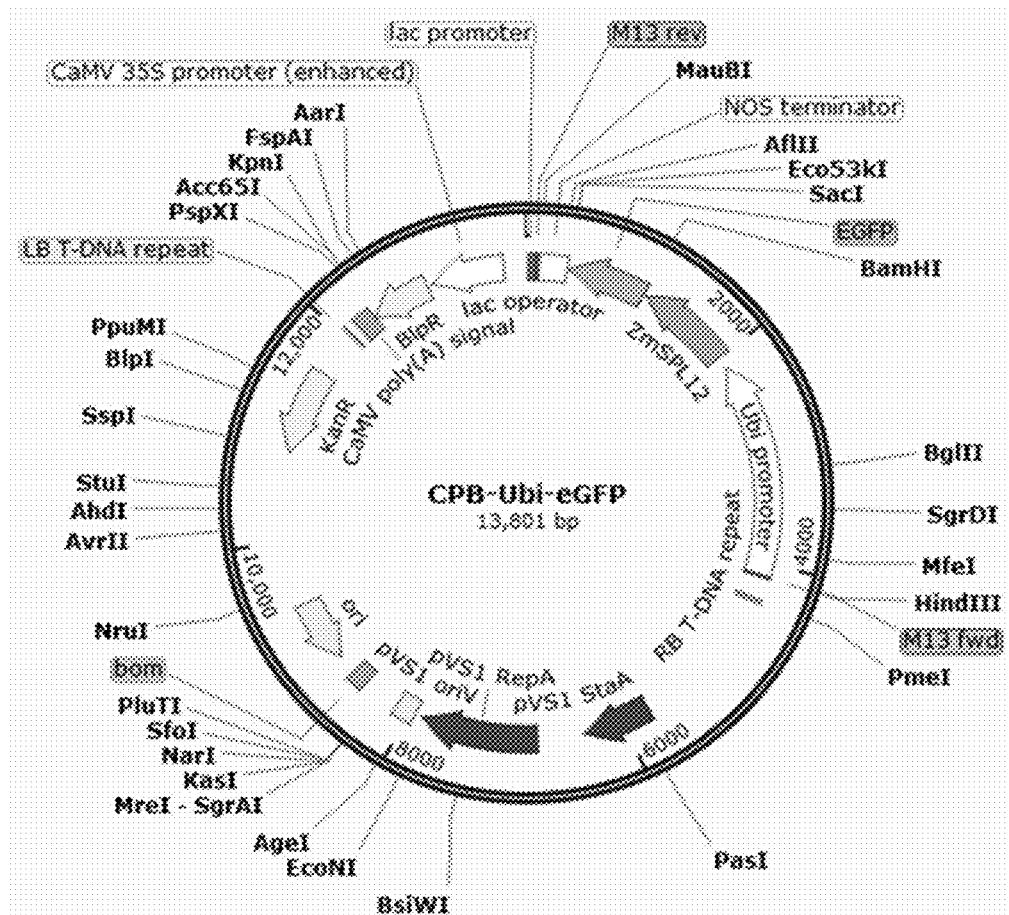
FIG. 1 is a schematic diagram of the ZmSBP12 gene overexpression vector Ubi::ZmSBP12-eGFP.
Figure 2:
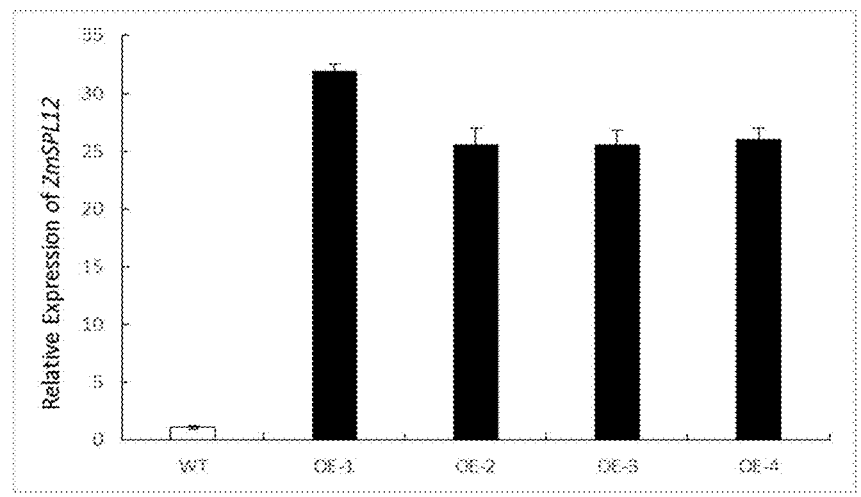
FIG. 2 shows the results of quantitative polymerase chain reaction (qPCR) detection of the ZmSBP12 gene in homozygous transgenic plants.

The present disclosure will be further described below in conjunction with specific examples, and the advantages and features of the present disclosure will become clearer from the description. However, these examples are only exemplary and do not constitute any limitation to the scope of the present disclosure. Those skilled in the art should appreciate that modifications and substitutions can be made to the details and forms of the present disclosure without departing from the spirit and scope of the present disclosure, but these modifications and substitutions fall within the protection scope of the present disclosure.

Unless otherwise specified, the experimental methods used in the examples are conventional methods.

The materials, reagents, and the like used in the examples are all commercially available unless otherwise specified.

The *Zea mays* L. inbred line "Xiang249" in the examples is publicly available from the Biotechnology Research Institute (BRI), Chinese Academy of Agricultural Sciences (CAAS).

EXAMPLE 1

Acquisition of a ZmSBP12 Gene and Construction of a Mutant ZmSBP12-OE

I. Acquisition and Modification of the ZmSBP12 Gene

The total RNA of a plant of a B73 inbred line at a V2 stage was extracted by the Trizol method, and reverse-transcribed with reference to the instruction of a reverse transcription kit. Since the ZmSBP12 gene was a *Zea mays* L. SQUAMOSA-PROMOTER BINDING PROTEIN-LIKE (SPL) transcription factor regulated by miR156, a miR156 regulatory site (CATGCTCTCTCTCTTCTGTCA) needed to be modified such that miR156 failed to recognize and cleave ZmSBP12.

A modification method was as follows: The primers 6827-F1/R1: GTTTGGTGTTACTTCTGCAGATG-GAGTGGACGGCCCCGAA/GCTGAGCAGGCTCAGG GCATGCTGAAGATCCGCTGCTC (as shown in SEQ ID NO: 8) were used to conduct the first round of PCR amplification with cDNA obtained from the reverse transcription as a template to obtain a fragment 1. The primers 6827-F2/R2: GCCCT-GAGCCTGCTCAGCGCCGGCGCTTGTGGACTGCCT-GATT/TGCCACCACCGGAT CCATTTATCTGGTTTA-CACCAAAGAAA (as shown in SEQ ID NO: 9) were used to conduct the second round of PCR amplification with cDNA obtained from the reverse transcription as a template to obtain a fragment 2. The primers 6827-F1/R2: GTTTGGTGTTACTTCTGCAGATG-GAGTGGACGGCCCCGAA/TGCCACCACCGGATCC ATTTATCTGGTTTACACCAAAGAAA (as shown in SEQ ID NO: 10) were used to conduct the third round of PCR-overlap PCR with a mixture of the fragment 1 and fragment 2 as a template to obtain a coding sequence (SEQ ID No: 6) of a site-modified ZmSPL12 gene.

II. Creation and Biological Characteristics of a Mutant ZmSBP12-OE

1. Construction of a ZmSBP12 Overexpression Vector pCAMBIA-Ubi::ZmSBP/2-eGFP

A DNA molecule shown in SEQ ID No: 2 in the Sequence Listing was inserted between PstI and BamHI restriction sites of the modified pCAMBIA vector through homologous recombination to obtain a ZmSBP12 overexpression vector pCAMBIA-Ubi::ZmSBP12-eGFP. The vector was sequenced. Sequencing results showed that the vector pCAMBIA-Ubi::ZmSBP12-eGFP was obtained by inserting a DNA molecule shown in SEQ ID No: 2 in the Sequence Listing between the PstI and BamHI restriction sites of the modified pCAMBIA without changing the remaining part of the modified pCAMBIA vector.

2. Acquisition of a Recombinant Bacterial Strain

The ZmSBP12 overexpression vector pCAMBIA-Ubi::ZmSBP12-eGFP obtained in step 1 was transformed into A. tumefaciens EHA105 through electric shock on a clean bench to obtain a recombinant strain pCAMBIA-Ubi::ZmSBP12-eGFP/EHA105, which could be transformed into a Xiang249 WT immature embryo callus.

3. Construction of a Mutant ZmSBP12-OE

A genetic transformation method of infecting an immature Zea mays L. embryo with A. tumefaciens includes: (1) preparation of an A. tumefaciens infection solution; (2) infection and co-cultivation, where the immature Zea mays L. embryo was infected with the infection solution, and after the infection was completed, the immature Zea mays L. embryo was cultivated in a co-cultivation medium in the dark with a scutellum facing upward; (3) screening, subcultivation, and plant regeneration; (4) induction; (5) differentiation; (6) rooting; and (7) seedlings were exercised, and then transferred to and planted in a field to obtain $T_0$-generation transgenic Zea mays L.

With reference to the above method, the mutant Ubi::ZmSBP12-eGFP was obtained with the DNA molecule shown in SEQ ID No: 6 in the Sequence Listing.

4. Identification of the Transgenic Mutant ZmSBP12-OE

Plants were sprayed with a 1/1,000 (V/V) Basta solution for screening and identification. If a plant is a negative plant (without transgenic ingredients), leaves on the plant will wither on day 3 after the Basta solution is sprayed. If a plant is a positive plant, the leaves on the plant (with transgenic ingredients) do not change.

5. Identification of Drought Resistance of the Mutant ZmSBP12-OE

Figure 3:
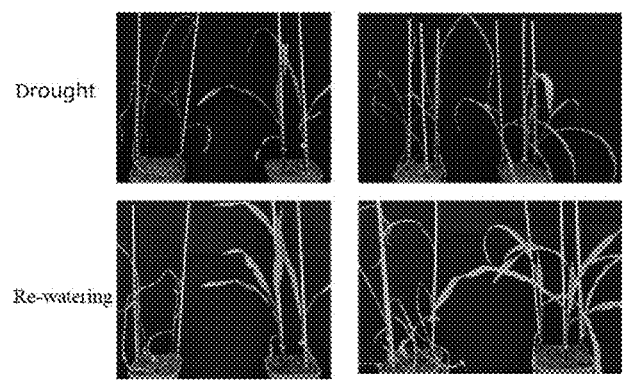
FIG. 3 shows the performance of WT and mutant ZmSBP12-OE after drought treatment.

The mutant ZmSBP12-OE and WT were cultivated in a light incubator (14 h light and 10 h dark; 28° C. in the light and 22° C. in the dark) until two true leaves and one apical bud grew, then subjected to drought treatment until all leaves of the WT withered, then rehydrated and further cultivated for 2 d, and the survival rate was counted. Results showed that the mutant ZmSBP12-OE exhibited drought resistance significantly higher than the drought resistance of the WT (FIG. 3).

6. Morphological Characteristics of the Mutant ZmSBP12-OE

Figure 4:
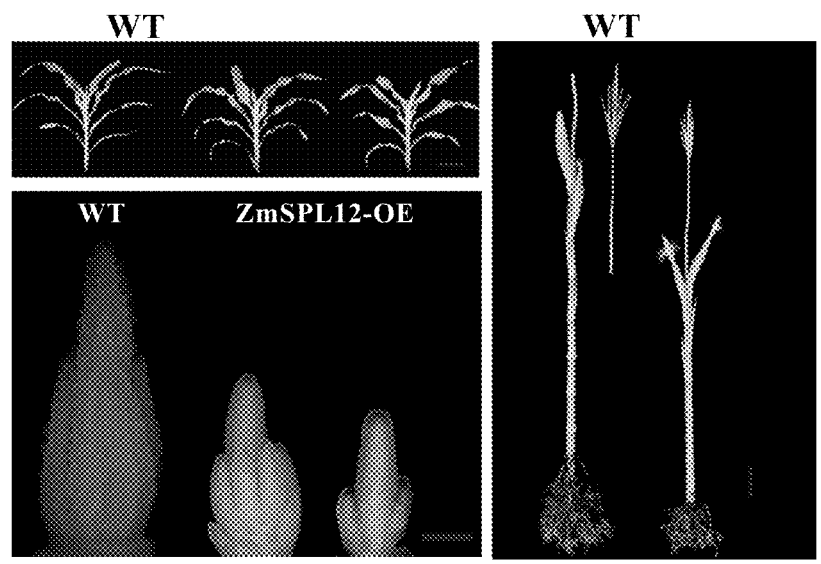
FIG. 4 shows the morphological characteristics of homozygous mutant ZmSBP12-OE, where the mutant ZmSBP12-OE is compared with the WT under natural sunlight conditions: At the 8 unfolded-leaf stages, the plant height is slightly low and leaf spacing is reduced in the mutant. When the WT SAM reaches the floret differentiation stage, the mutant has just reached the spikelet differentiation stage.
Figure 5:
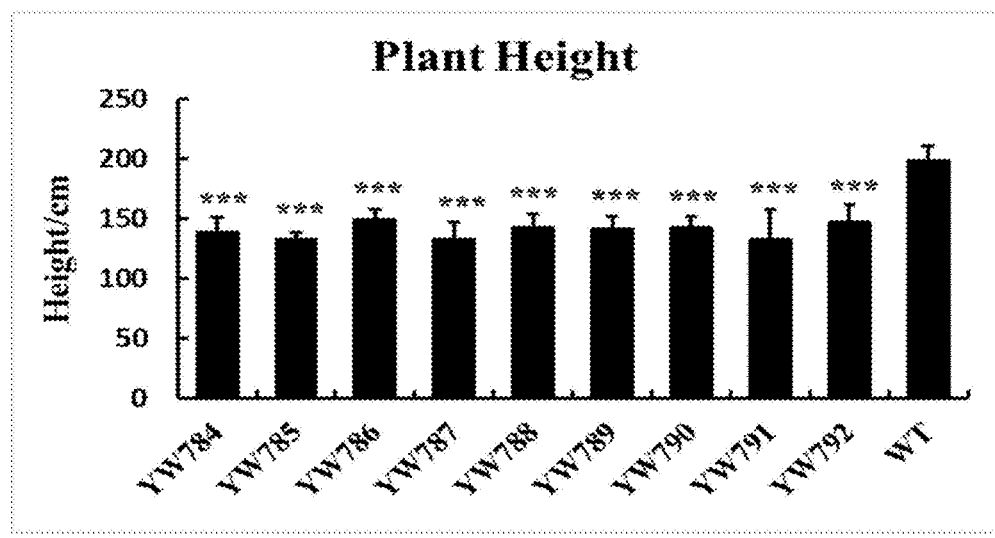
FIG. 5 shows the plant height statistics of mutant ZmSBP12-OE and WT under natural sunlight conditions, where it can be seen from the statistical data that the plant height of the mutant ZmSBP12-OE is significantly lower than the plant height of the WT. YW784-785 represents OE-1, YW786-788 represents OE-2, YW789-790 represents OE-3, and YW791-792 represents OE-3. Based on a sample size N≥30, P≤0.005 is regarded as reaching an extremely-significant level.
Figure 6:
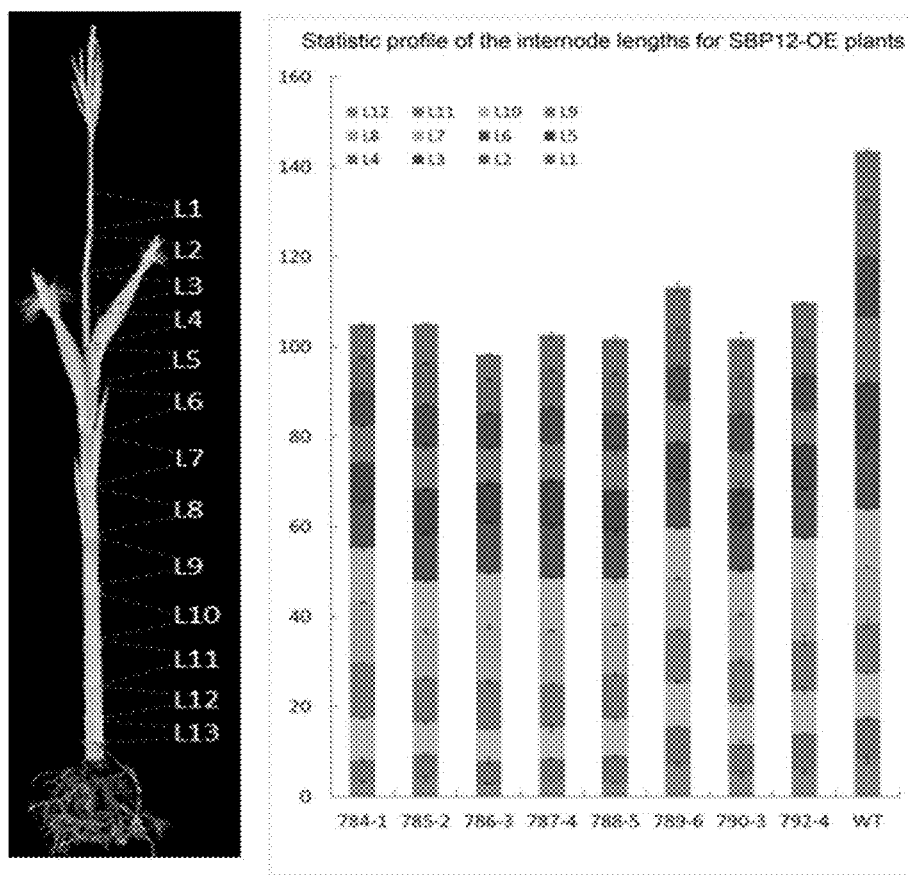
FIG. 6 shows the length statistics of aboveground nodes of mutant ZmSBP12-OE and WT under natural sunlight conditions.
Figure 7:
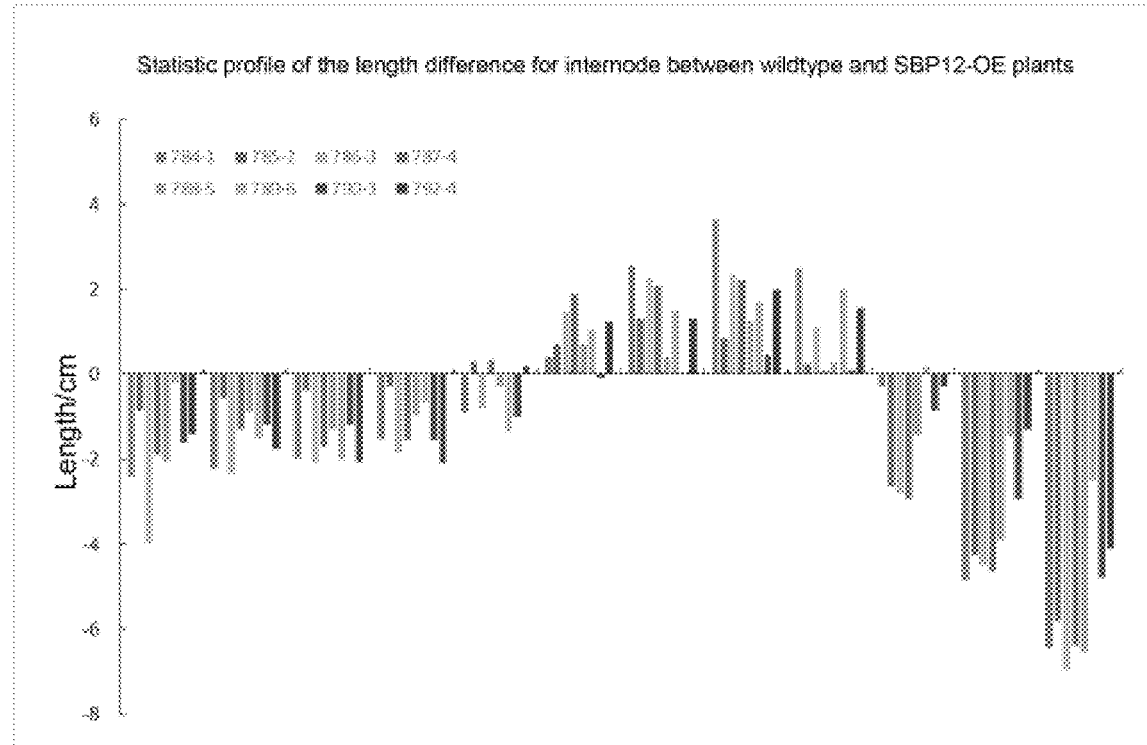
FIG. 7 shows the changes in lengths of aboveground nodes of mutant ZmSBP12-OE compared with WT under natural sunlight conditions (it can be seen that the first 1 to 3 aboveground nodes are most significantly reduced, indicating that this phenotype is closely related to lodging resistance).

Under natural sunlight conditions, at the 8 unfolded-leaf stage, the plant height of the mutant ZmSBP12-OE was slightly lower than the plant height of the WT, and leaf spacing was reduced (FIG. 4). The growth of plants was delayed. When the WT SAM reached the floret differentiation stage, the mutant had just reached the spikelet differentiation stage (FIG. 4), and the plant height of the mature plant was decreased. Under the same growth conditions, the lengths of aboveground nodes of the mutant ZmSBP12-OE and WT were counted, and it was found that most of the internodal lengths of the mutant were decreased compared with the WT, but internodal lengths of some nodes were slightly larger than that of the WT. In addition, the changes in lengths of aboveground nodes of the mutant ZmSBP12-OE compared with the WT were counted, and it was found that the first 1 to 3 aboveground nodes of the mutant were most significantly decreased. Production practice and research have shown that the stalk breaking of Zea mays L. occurs at the first 1 to 3 aboveground nodes, and the stalk breaking can cause a reduction in corn output or even no harvest, which is closely related to lodging resistance.

7. The Overexpression of ZmSBP12 Can Reduce a Hybrid's Plant Height and Ear Height.

Figure 8A:
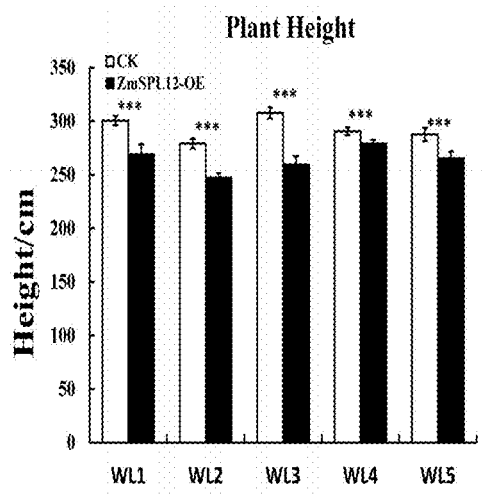
FIGS. 8A-8B show the plant height and ear height statistics of F1 populations obtained from the combination of WT and ZmSBP12-OE with backbone parents (WL1, WL2, WL3, WL4, and WL5) (it can be seen that ZmSBP12-OE can also significantly reduce the plant height and ear height of a hybrid).
Figure 8B:
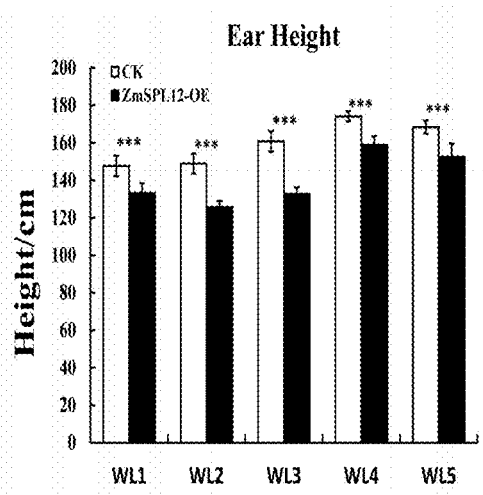

The WT and mutant ZmSBP12-OE were each combined with each of the backbone parents (WL1, WL2, WL3, WL4, and WL5) to obtain F1 populations. A phenotype was observed in Langfang, where the planting density was 6,000 plants/mu and the management mode was the same as the general Zea mays L. field management mode. After the plant type remained unchanged (30 d after pollination), a phenotype was determined. Statistical results are shown in FIGS. 8A-8B. The results show that the overexpression of the ZmSBP12 gene can reduce a hybrid's plant height and ear height, indicating that the increased expression of the ZmSBP12 gene can improve the lodging resistance.

In summary, after the ZmSBP12 gene is over-expressed in Zea mays L., the drought resistance is increased and the plant and ear heights are decreased in the Zea mays L. mutant, indicating that the ZmSBP12 gene plays a crucial role in the drought resistance and plant type (plant height) of Zea mays L. and has a high breeding application value.

What is claimed is:

1. A method for improving lodging resistance of a *Zea mays* plant comprising:
   (i) constructing a recombinant plant expression vector carrying a ZmSBP12 coding sequence as set forth in SEQ ID NO: 2 or SEQ ID NO: 6 which encodes the ZmSBP12 protein as set forth in SEQ ID NO:1, wherein said recombinant plant expression vector comprises inserting the nucleotide sequence as set forth in SEQ ID NO: 2 or SEQ ID NO: 6 between PstI and BamHI restriction sites of a modified pCAMBIA vector to obtain a ZmSBP12 overexpression vector pCAMBIA-Ub1::ZmSBP12-eGFP;
   (ii) transforming said constructed recombinant plant expression vector into a *Zea mays* plant tissue or a *Zea mays* plant cell;
   (iii) overexpressing said ZmSBP12 protein in the transformed *Zea mays* plant tissue or the *Zea mays* plant cell;
   (iv) regenerating transformed *Zea mays* plants overexpressing said ZmSBP12 protein from said transformed *Zea mays* plant tissue or the *Zea mays* plant cell of step (iii); and
   (v) selecting a transformed *Zea mays* plant from said regenerated transformed plants of step (iv) that overexpresses said ZmSBP12 protein and exhibits increased lodging resistance as compared to a control or wild-type *Zea mays* plant that is not transformed with said constructed recombinant plant expression vector and is grown under identical growth conditions.

2. The method according to claim 1, wherein said method comprises transforming the ZmSBP12 overexpression vector pCAMBIA-Ub1::ZmSBP12-eGFP into *A. tumefaciens* EHA105 through electric shock to obtain a recombinant strain pCAMBIA-Ubi::ZmSBP12-eGFP/EHA105.

3. The method according to claim 2, wherein the method further comprises transforming the recombinant strain pCAMBIA-Ub1::ZmSBP12-eGFP/EHA105 into an immature *Zea mays* embryo callus.

4. The method according to claim 1, wherein the selected transformed *Zea mays* plant of step (iv) further exhibits reduced plant height or reduced ear height as compared to said control.

5. The method according to claim 1, wherein the coding sequence is set forth in SEQ ID NO: 2.

6. The method according to claim 1, wherein the coding sequence is set forth in SEQ ID NO: 6.

* * * * *